United States Patent
Fröse

(10) Patent No.: US 8,576,396 B2
(45) Date of Patent: Nov. 5, 2013

(54) CELL CONSTRUCTION FOR LIGHT SCATTER DETECTORS HAVING SELF-FOCUSING PROPERTIES

(75) Inventor: Diethelm Fröse, Berlin (DE)

(73) Assignee: Postnova Analytics GmbH, Landsberg (DE)

( * ) Notice: Subject to any disclaimer, the term of this patent is extended or adjusted under 35 U.S.C. 154(b) by 88 days.

(21) Appl. No.: 13/129,933

(22) PCT Filed: Nov. 19, 2009

(86) PCT No.: PCT/DE2009/001684
§ 371 (c)(1),
(2), (4) Date: Jun. 13, 2011

(87) PCT Pub. No.: WO2010/057490
PCT Pub. Date: May 27, 2010

(65) Prior Publication Data
US 2011/0242535 A1  Oct. 6, 2011

(30) Foreign Application Priority Data

Nov. 19, 2008 (DE) .................. 10 2008 058 607

(51) Int. Cl.
*G01N 21/00* (2006.01)
(52) U.S. Cl.
USPC ....................................... 356/338
(58) Field of Classification Search
USPC ......................... 356/445, 335–343
See application file for complete search history.

(56) References Cited

U.S. PATENT DOCUMENTS

| | | | | |
|---|---|---|---|---|
| 4,273,443 A | * | 6/1981 | Hogg | 356/343 |
| 4,616,927 A | * | 10/1986 | Phillips et al. | 356/338 |
| 4,728,190 A | * | 3/1988 | Knollenberg | 356/336 |
| 4,997,278 A | * | 3/1991 | Finlan et al. | 356/128 |
| 5,305,073 A | * | 4/1994 | Ford, Jr. | 356/338 |
| 6,052,184 A | | 4/2000 | Reed | |
| 6,120,734 A | * | 9/2000 | Lackie | 422/68.1 |
| 6,573,992 B1 | * | 6/2003 | Drake | 356/338 |
| 6,819,421 B1 | * | 11/2004 | Mead et al. | 356/338 |
| 2002/0064800 A1 | | 5/2002 | Sando et al. | |
| 2005/0239210 A1 | | 10/2005 | Iida | |
| 2007/0210269 A1 | * | 9/2007 | Sonehara et al. | 250/576 |
| 2012/0140221 A1 | * | 6/2012 | Salton | 356/337 |

FOREIGN PATENT DOCUMENTS

| | | |
|---|---|---|
| EP | 0 182 618 B1 | 11/1990 |
| EP | 0 626 064 B1 | 11/2001 |
| EP | 1 489 403 A1 | 12/2004 |
| EP | 1 515 131 A1 | 3/2005 |
| EP | 1 801 560 A1 | 6/2007 |
| JP | 62285043 A * | 12/1987 |
| JP | 2006-189292 A | 7/2006 |
| JP | 2007-271365 A | 10/2007 |
| WO | PCT/DE2009/001684 | 4/2010 |

* cited by examiner

*Primary Examiner* — Gregory J Toatley
*Assistant Examiner* — Shawn Decenzo
(74) *Attorney, Agent, or Firm* — Hodgson Russ LLP

(57) ABSTRACT

The invention relates to a device and to a method for measuring the scattered light about molecules present in a suspension, wherein the suspension is fed through a measurement cell. The measurement cell is produced as a segment of a curved surface, particularly an ellipsoid, a hyperbolic shape, a parabolic shape, or a circle, and comprises a curved and a flat surface. Light-sensitive detectors are disposed about the curved surface and capture the scattered light.

13 Claims, 2 Drawing Sheets

CELL CONSTRUCTION FOR LIGHT SCATTER DETECTORS HAVING SELF-FOCUSING PROPERTIES

FIELD OF THE INVENTION

The invention relates to a device for measuring the light scattering properties of a suspension which is fed through a sample cell and is illuminated by a collimated light beam, as well as to a method for measuring the light scattered on molecules present in a suspension.

BACKGROUND OF THE INVENTION

The measurement of the static light scattering is used for the characterisation (size, mass, form and structure) of molecules or colloidal substances. This is an absolute quantification which manages without any previous calibration or use of standard samples. A sample is illuminated with a collimated light beam, and the scattered light is measured at different scattering angles.

The principle of light scattering is widespread in nature. It can be observed, e.g. at sunset or when dust particles become visible. Light beams strike a strongly scattering medium, and are deflected from their geometrically prescribed path by particles. The intensity of the light beams is weakened here by absorption and scattering. The scattering is the basis for different physical phenomena such as e.g. deflection, refraction and reflection.

Scattering can be sub-divided into non-elastic, quasi-elastic and elastic scattering which differ in their frequency shift. With non-elastic scattering a frequency shift of approximately $10^{11}$ to $10^{13}$ Hz occurs. With quasi-elastic scattering, with which light additionally interacts with translation and rotation quanta of a molecule, a frequency shift of 10 to $10^6$ Hz occurs. With elastic light scattering (e.g. static light scattering) there is no change to the wavelength (also called coherent scattered radiation). The underlying principle of light scattering can be demonstrated with a very small, optically isotropic gas molecule. The electrons of the molecule are caused to vibrate through the incidence of the electromagnetic wave with the frequency of the stimulating light source. The oscillating dipole thus produced in turn emits electromagnetic radiation of the same frequency, the intensity of the radiation depending on the strength of the induced dipole, i.e. the more polarisable the molecule, the stronger the dipole and the greater the intensity of the emitted radiation.

If a sample, for example a suspension, in which a number of macromolecules are located, is illuminated with a collimated light beam, every macromolecule emits radiation. The sum of the intensities of the emitted radiation is in proportion to the concentration of the macromolecules in the suspension and of the molar mass of the molecules. Furthermore, the size of the molecules contained in the colloid can be calculated from the angle dependency of the scattered light intensities since the light scattered at the different scattering centres in the macromolecule interferes and produces an angle-dependent scattering pattern. The average values of the particles located in the cell are respectively determined here. In the prior art measuring instruments are described which measure the scattering properties of colloidal liquids and use them for the characterisation of the material properties. EP 0 182 618 B1 discloses a device which describes the measurement of the static light scattering by means of a sample cell. The sample cell can be coupled to a chromatographic construction so that the particles, separated according to size, flow through the sample cell. For this a round glass cell is provided with a longitudinal bore hole through which a flow of liquid with the contained particles is fed and is illuminated with a laser beam. Detectors, which collect the scattered light, are arranged around the round glass cell at different angles. In order to determine the angle dependency every detector may only collect a small angle range. Therefore, with this instrument it is necessary to reduce the detected range in the bore hole to a few nanoliters by means of apertures, and this increases noise and interference. This inevitably leads to a reduction in sensitivity.

This technology was described first of all in U.S. Pat. No. 4,616,927 and in EP 0 182 618. However, they only disclose the measurement of the scattered light at a number of different angles. The scattering range observed is limited to a few nanoliters by means of apertures. EP 0 626 064 is a further development where measurements are taken at 2 angles, the light scattered at 15 degrees being collected by means of a lens and aperture system.

In U.S. Pat. No. 6,052,184 the scattered light is collected by means of fibre optics, the latter also only observing a very small liquid range however. The flow of liquid is guided here perpendicularly to the incident light beam. In EP 1 515 131 it is described how the volume of liquid can be minimized by using a second flow of liquid, the volume of liquid observed also being limited, however.

It is a disadvantage with the devices disclosed in the prior art that the volume of liquid observed is extremely limited by aperture systems or the use of fibre optics which are brought close to the scattering centre in order to obtain a good angle resolution and to keep scattered light away from air/glass/medium interfaces. Therefore the sensitivity of the method is reduced.

SUMMARY OF THE INVENTION

The problem underlying the invention is to provide a measuring device which does not have the disadvantages given in the prior art and which achieves improvement of the measuring sensitivity.

The problem is solved by the independent claims. Advantageous embodiments of the invention are given by the subclaims.

Accordingly, the invention comprises a device for measuring the light scattering properties of a suspension which is fed through a sample cell and is illuminated by a monochrome collimated light beam, the sample cell having a channel which permits the feed and discharge of the suspension, and which allows a monochrome collimated light beam to pass in, pass through and pass out in the direction of its length, wherein the cell geometry of the sample cell has a curved surface, and the sample cell is formed from transparent material and focuses scattered light by the curved surface of the sample cell, and wherein light-sensitive detectors are arranged so that they collect the light scattered by a suspension and which passes through the channel and the transparent material of the sample cell.

It was totally surprising that the deficiencies of the prior art could be eliminated by the device according to the invention. The invention relates to a device which serves to measure the light scattering properties of a suspension which is fed through a sample cell and is illuminated by a monochrome collimated light beam. The coherence length of the light beam can preferably be greater than the maximum size of the molecules to be measured, molecules with a size of 10 nm to 1000 nm and a molecular mass of 1000 Da to $1 \times 10^9$ Da being preferably characterized. The cell geometry of the sample cell has a curved surface. The sample cell surrounds a channel which permits the feed and discharge of the suspension. Furthermore, the channel allows a collimated light beam to pass in, pass through and pass out in the direction of its length. The light scattered by the molecules present in the suspension passes through the transparent material of the sample cell and is focused by the curved surface of the sample cell according to the invention such that light-sensitive detectors arranged around the sample cell collect the light which passes through the channel and the transparent material of the sample cell. The irradiated molecules scatter the light in all directions, the scattering intensity at different angles depending upon the size of the molecules.

In a preferred embodiment a device for measuring the light scattering properties of a suspension which is fed through a sample cell and is irradiated by a monochrome collimated light beam is provided, the sample cell formed from transparent material having a channel which includes at least two openings, and the sample cell being formed as a segment preferably of an ellipsoid, a hyperbolic shape, a parabolic shape or of a circle, and having a curved surface, light-sensitive detectors being arranged around the sample cell, preferably around the curved surface. It was totally surprising that the preferred shape of the sample cell improves in particular the measurement of colloidal substances and reduces background noise. Within the framework of the invention a segment here preferably denotes a partial area which preferably has a curved surface and a flat surface lying opposite the curved surface. Within the framework of the invention a curved surface or side preferably denotes a curvature which has a change in direction for each unit of length, i.e. an outwardly quadratically increasing deviation of the surface from its tangential plane preferably occurs. This preferred embodiment of the sample cell makes in particular a compact and inexpensive design possible. An advantageous sample cell of this type is shown as an example in FIG. 1.

Within the framework of the invention a suspension denotes a heterogeneous mixture in which solids (molecules) are distributed within a fluid.

Within the framework of the invention a channel denotes a recess in the cell body through which the medium being investigated flows and in which it is illuminated by a monochrome collimated light beam which preferably consists of light beams running in parallel and is monochrome. The coherence length of the light is preferably greater than the diameter of the macromolecules being investigated.

Advantages are gained by the device according to the invention in comparison to the prior art. The device thus makes it possible to collect all of the scattered light which passes from the colloidal suspension through the sample cell and is collected by the detectors. The scattered light of substantially all of the suspension present within the sample cell is thus collected, by means of which a scattered volume in the microliter range can be measured. Sample cells described in the prior art only have a scattered volume in the nanoliter range.

It is a further advantage of the device according to the invention that due to the increased scattered volume the intensity of the scattered light is increased because the intensity is in proportion to the scattered volume. An increase in intensity results in a strengthening of the signal and leads to improved sensitivity and enables measurement of colloidal suspensions in low concentrations.

A further advantage of the device according to the invention is the reduction of the background noise. The particles in the suspension move in reciprocal dependency upon their size in random directions. This movement results in a measuring error when measuring a colloidal suspension which is called noise and can distort the measurement result. The smaller the volume of the sample cell being observed, the less molecules are contained in the suspension, and the stronger is the temporal fluctuation of the scattered radiation. This results in an increase in noise. With an increase in the volume to be measured, the number of molecules in the sample cell is increased, and the effect of the noise is reduced because more scattered beams pass to the detectors, and so the signals can be averaged.

The invention thus resolves a long-standing problem of the prior art and makes it possible to collect all of the scattered light and so leads to improved sensitivity.

It is preferred if the geometry of the sample cell preferably has a segment of a curved surface, in particular of an ellipsoid, a hyperbolic, a parabolic shape or the form of a circle.

One advantageous embodiment of the subject matter of the invention makes provision such that the sample cell is produced from glass, polymer or a combination of both or a liquid which has a higher refractive index than the suspension or air being measured. A polymer denotes a chemical compound which consists of chains or branched molecules which are made up of identical or similar units. Examples of these are polymers made of polyethylene, polypropylene, polyvinyl chloride, polymethyl methacrylate, polyester or polyurethane. The refractive index, previously the index of refraction or the refractivity, is a material constant and describes the propagation of the light, i.e. electromagnetic waves, in an optically dense medium. It can be determined from the ratio between the phase velocity of the light in a vacuum and its phase velocity in the respective medium. Therefore e.g. the refractive index for visible light in a vacuum is exactly 1, for air at sea level 1.000292, for quartz glass 1.46 and for polymers approximately 1.5. The embodiment according to invention makes it possible for the scattered beams to be refracted such that they are focused in a point at which light-sensitive detectors are installed. Therefore the scattered radiation scattered away from the detectors can also be focused into the latter. Consequently it is made possible by the advantageous embodiment for the light-sensitive detectors to collect substantially all of the scattered beams coming from the sample cell.

Provision is advantageously made such that the sample cell has an optically polished surface and a cross-section of the sample cell is curved in the plane of the channel and the channel extends along an axis, the channel being shorter than the smallest diameter of the curved surface. The curved surface, through which the light passes out, is to be polished using standard methods in order to minimize angular distortions or scattering on the optical interfaces. A circle axis is defined as a stretch which is produced by connecting two points located on a circle. A polished surface is achieved by conventional polishing methods. The surface of e.g. quartz glass can thus be processed by flame polishing and mechanical polishing Polishing by means of laser beams is also possible.

By means of the preferred configuration of the sample cell it is possible for the light scattered by the molecules to be refracted towards the axis of incidence at the suspension/sample cell interface because the refractive index of the sample cell is preferably greater than the refractive index of the medium. In other words, light beams which have been scattered at a specific angle within the channel run parallel to one another through the sample cell. By means of the preferred embodiment the light beams scattered (horizontally) in the plane of the channel are focused onto a point outside of the sample cell at the sample cell/surrounding medium interface where the light-sensitive detectors are arranged. In this way it is possible to collect all of the light scattered in the horizontal plane, by means of which the sensitivity of the device is significantly increased. Furthermore, by means of the embodiment it is also possible for scattered beams, which are scattered away from the detectors, to be focused into the latter. Substantially more scattered light can thus be collected by the light-sensitive detectors.

In one preferred embodiment the sample cell has a polished surface, and a cross-section of the sample cell is curved in the plane perpendicular to the plane of the channel. Since the sample cell has a curve not only in the plane of the channel (horizontal), but also in the plane perpendicular to the plane of the channel (vertical) the beams running in parallel through the sample cell are focused in a point outside of the sample cell upon reaching the outside of the sample cell. Therefore vertical and horizontal focusing of the scattered beams preferably takes place, and all of the beams scattered below an angle are focused in a point outside of the sample cell. By means of the preferred embodiment all of the scattered light of the sample cell is collected and the scattered volume measured is increased, and this leads to improved sensitivity.

In a further preferred embodiment light-sensitive detectors are arranged over the curved surface or side in a plane with the channel (horizontal) in order to collect the light scattered by the irradiated suspension and focused by means of the sample cell. A detector is a device described in the prior art which converts an incident light intensity into electric signals which takes place e.g. by means of light-sensitive diodes or photomultipliers and forwards them to processing equipment which converts the measured signals into the desired units. By means of the arrangement of the detectors over the curved surface it is possible for scattered light, which has not been generated by the suspension but was produced e.g. on the side edges of the channel, to not pass into the detectors. The inflow of disruptive scattered light into the measurement is thus prevented and measuring errors reduced. Furthermore, by means of the preferred embodiment a compact and material-saving construction can be realized since light-sensitive detectors are only arranged on one side, namely the curved side.

Furthermore, it is preferred if light is focussed on the curved surface or side in a plane perpendicular to the plane of the channel, preferably by means of the curved side of the surface or by means of Fresnel lenses and/or cylindrical lenses, and is collected by light-sensitive detectors. The focusing of the scattered light beams at the sample cell/surrounding medium interface is preferably achieved by the curvature of the surface. The sample cell is produced from a material with a higher refractive index than air by means of which the light beams passing out are focused. The focusing can also be implemented with the aid of Fresnel lenses and/or cylindrical lenses. Fresnel lenses are compact optical lenses which are characterized by a division into annular steps. By means of the steps a constant focal width is achieved, i.e. the distance of the focal point or the focus does not change. The characteristic shape of the Fresnel lenses makes it possible to save weight due to which they are used in applications where the weight is crucial. Cylindrical lenses have different curvatures in two directions perpendicular to one another, i.e. cylindrical lenses are preferably sections of a cylinder. As a further embodiment, both lens types can execute the focussing of the light beams scattered by the suspension and focus the latter into the detectors. By means of the weight-saving shape of the lenses a compact embodiment is realized, and additionally the maintenance of the preferred embodiment is simplified by the lenses since the latter can easily be changed by the person skilled in the art. The preferred embodiments lead to the scattered beams being focussed in detectors at the sample cell/surrounding medium interface. By means of this arrangement it is possible to collect all of the scattered light and no scattered light is lost. Improved sensitivity is the result.

In a further preferred embodiment of the invention the light-sensitive detectors, which collect the scattered light, have an aperture system which defines the angle range to be observed provided the focus lies within the aperture. An aperture system describes a device fitted to the detectors which only allows collection of specific beams. Thus, beams reaching the detectors at an angle which is not to be used for the measurement are excluded by the aperture system. The range of the beams to be measured (the angle range) is set by the aperture system. Preferably the aperture is fitted in front of the detector exactly in the focus of the scattered light and serves to minimize the detected angle range. Furthermore, beams which are not exactly in the focus are masked by the apertures. By means of this arrangement all of the scattered light which is produced in the channel by the irradiation of the suspension is collected, and so the sensitivity of the further embodiment of the invention is improved. In addition the use of an aperture system enables adaptation to properties of the suspension being measured, such as e.g. highly concentrated suspensions, suspensions with large or small molecules, since this can easily be set by the person skilled in the art.

In a preferred embodiment there are no detectors arranged on the side lying opposite the curved surface or side, but a light-absorbing device is installed which absorbs light which is not to be collected by the detectors. Thus e.g. by means of the light-absorbing device scattered light which is produced on the feeds and discharges of the channel should not pass into the light-sensitive detectors. This scattered light would distort the measurement of the scattered beams which have been generated by the suspension being measured because one can no longer differentiate between scattered light to be measured and the scattered light not to be measured. Consequently the characterisation of the colloidal suspension would be based upon incorrect measurement data. For this reason the detectors are not arranged all the way round the sample cell. It is preferable for the detectors only to be arranged on one side of the sample cell, in particular on the side which is in the form of a curved surface, preferably a curved surface of a segment. By means of the preferred embodiment it is guaranteed that substantially all of the light scattered by the suspension is collected by the detectors, and in addition light, which does not derive from the light scattering of the suspension, is not collected by the detectors. A trap aperture is given as an example of this type of light-absorbing device which removes light not to be measured and so prevents distortion of the measurement result. Furthermore, coating the sample cell with an absorbent coloring can be advantageous.

In a further preferred embodiment the monochrome collimated light beam has a cross-sectional dimension that is smaller than that of the channel. A monochrome collimated light beam describes a monochrome light beam running in parallel. By means of the preferred embodiment it is guaranteed that no reflections are produced when the monochrome light beams running in parallel pass through the channel.

Furthermore, by using a monochrome collimated light beam it is guaranteed that no interference occurs and the scattered light beams do not affect one another.

The invention also relates to a method for measuring the light scattered on molecules present in a suspension, wherein
   a) a suspension is fed though a channel that extends along
      a circle axis through a sample cell, b) a collimated, monochrome light beam runs along this channel, c) the scattered light beams running in parallel pass the curved shape of the sample cell, d) are focussed by the polished, curved shape of the sample cell, e) and the detectors arranged horizontally and vertically to the channel collect the focussed light.

The method makes it possible to measure the scattered light which is produced by irradiating a colloidal suspension. For this purpose a colloidal suspension is fed through a channel that extends along a circle axis through a sample cell. A monochrome, collimated light beam runs along this channel and irradiates the suspension by means of which light is scattered by the colloidal components. The light beams scattered at a specific angle are refracted towards the axis of incidence at the suspension/sample cell interface and run in parallel through the sample cell. At the sample cell/surrounding medium interface the scattered beams running in parallel are focussed by the polished, curved shape of the sample cell. Light-sensitive detectors, which receive the focussed light, are arranged around the round or curved side of the sample cell. The detectors are located in the horizontal and the vertical plane, i.e. in a plane with the channel running through the sample cell and in a plane perpendicular to the plane of the channel. Therefore, substantially all of the light which is scattered by the suspension can be collected by the detectors. The light received by the detectors is preferably converted into electric signals and forwarded to processing equipment in order to calculate the desired properties, such as e.g. size and concentration. The method makes it possible to measure a large scattered volume which is directly in proportion to the intensity of the beams. A higher intensity correlates to a higher sensitivity because the scattered radiation of molecules, which are, for example, present in the suspension in a low concentration, is amplified and can be collected by the detectors. Furthermore, by increasing the scattered volume reduction of the noise is achieved. The noise is produced by random movements of the molecules in the suspension and the resulting temporal displacement of the scattered beams due to which interference occurs which makes it difficult to measure the scattered beams because light beams affect one another, i.e. they can be amplified or deleted. The method reduces the noise by increasing the scattered volume, by means of which more molecules are collected in the suspension and averaging of the scattered beams reduces the effect of the movement. Therefore, by means of the method a long-standing problem in the prior art is resolved. The sensitivity of the measurement is improved by collecting a larger scattered volume, and substantially all of the scattered light of the suspension being measured is collected by means of light-sensitive detectors. This is a simple and inexpensive method which determines properties of a colloidal suspension.

A preferred embodiment of the method is characterized in that the sample cell in the plane of the channel and in the plane perpendicular to the plane of the channel displays a curved surface. By means of this shape of the sample cell it is possible for the light beams scattered at an angle to be diffracted towards the axis of incidence at the suspension/sample cell interface and to run in parallel through the sample cell, and to be focussed in a point outside of the sample cell at the sample cell/surrounding medium interface. Detectors fitted at this point collect the scattered light. Therefore the preferred embodiment allows substantially all of the scattered light to be collected, by means of which sensitivity is increased.

A further embodiment of the method is characterized in that the light-sensitive detectors are arranged over the round side of the sample cell. The arrangement of the light-sensitive detectors over the curved side of the sample cell causes substantially the scattered light which is focussed by the sample cell to fall into the detectors and enables it to be used in order to calculate the properties of the colloidal suspension. Light beams which are produced at the feeds and discharges of the channel or reflections may not be collected by the detectors because the measurement result is distorted by these light beams and the colloidal suspension can not be determined correctly. In order to exclude light beams or reflections which are not to be measured from the measurement a light-absorbing device, such as e.g. a trap aperture or a light-absorbing coating, is advantageously installed on the side lying opposite the round side of the sample cell. Furthermore, the light-sensitive detectors are preferably equipped with an aperture system which defines the angle range to be measured. In this way accurate measurement of the light scattering is possible because substantially all of the scattered light coming from the sample cell is collected and used for the calculation of the properties of the colloidal suspension.

Further advantageous measures are described in the other sub-claims.

DESCRIPTION OF THE DRAWINGS

The invention will now be described as an example by means of figures, without, however, being restricted to the latter; these show as follows.

DETAILED DESCRIPTION OF THE INVENTION

Figure 1:
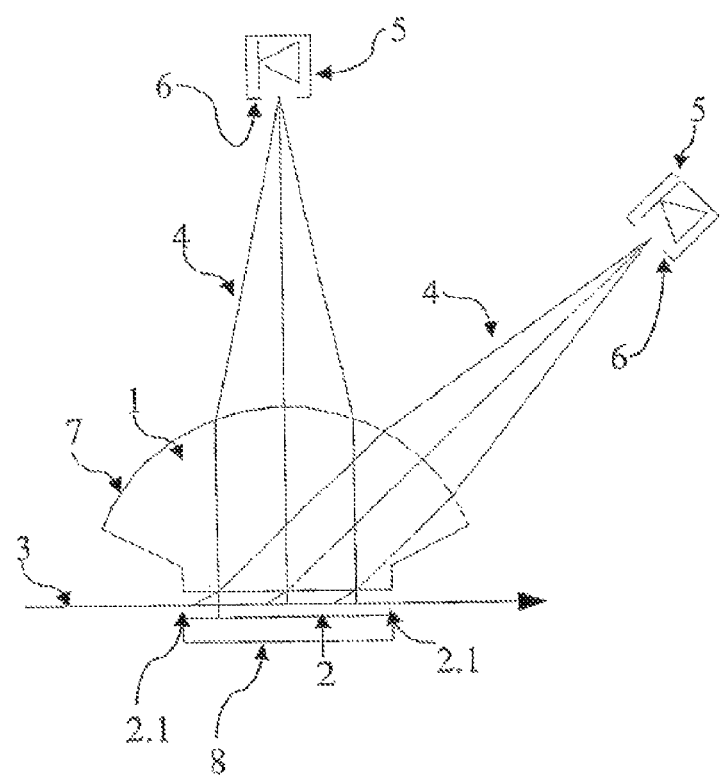
FIG. 1 A horizontal section through the cell geometry

FIG. 1 shows diagrammatically a horizontal section through the cell geometry. The sample cell 1 is preferably made of glass, polymer or a combination of both or a liquid which has a higher refractive index than air. A channel 2 is made in the sample cell 1 which has a curved surface 7, and the channel 2 extends along an axis through the sample cell 1. A cross-section of the sample cell 1 in the plane of the channel 2 and a cross-section in the plane perpendicular to the plane of the channel 2 displays a curved surface 7. There is fed through the channel 2 a colloidal suspension which is irradiated by a monochrome collimated laser beam 3. The laser beam 3 runs along the channel 2, the cross-section of the laser beam 3 being smaller than that of the channel 2. At the incidence of the light beams 3 onto the molecules of the suspension, the light is scattered in all directions depending on the size of the molecules. The scattered beams 4 are refracted towards the axis of incidence at the suspension/sample cell interface and run in parallel through the sample cell 1. When the scattered beams 4 reach the curved, polished surface in the horizontal plane, i.e. in the plane of the channel, the beams are focused on a point where light-sensitive detectors 5 are fitted. Accordingly all of the beams 4 scattered at a specific angle are focussed by the curved surface 7 so that substantially all of the scattered light 4 of the suspension is collected by the light-sensitive detectors 5. Scattered beams 4, which are scattered away from the detectors 5, are also focussed into the latter by the round surface. The light-sensitive detectors 5 process the incoming signals, convert the latter into electric signals, and forward the latter to corresponding processing equipment. An aperture system 6 is installed on the light-sensitive detectors 5. The aperture system 6 makes it possible to restrict the scattered beams 4 to be collected by means of an aperture which only allows light beams which have been scattered at a defined angle to pass into the light-sensitive detectors 5.

Reflections or scattered light which occurs to the side from the feeds and discharges of the channel 2.1 can thus be prevented from being collected by the light-sensitive detectors 5 and being used for the calculation. The measurement result would be distorted by this disruptive scattered light. The sample cell 1 is advantageously in the form of a segment, i.e. a non-curved surface 8 is preferably arranged opposite the curved surface or side 7.

Figure 2:
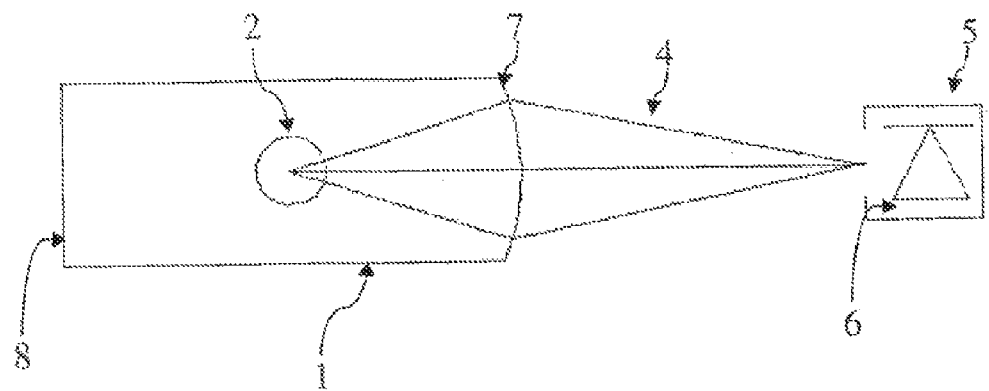
FIG. 2 A vertical section through the cell geometry.

FIG. 2 is a diagrammatic illustration of a vertical section through the cell geometry. A colloidal suspension, which is irradiated by a light beam 3, flows through the channel 2 made in the sample cell 1. In the plane perpendicular to the plane of the channel the sample cell 1 has a curved surface, and the channel 2 extends along an axis. Therefore the sample cell 1 displays a curved surface in the plane of the channel 2 (horizontal) in the plane perpendicular to the plane of the channel 2 (vertical). Therefore the sample cell 1 has a curved side. There is arranged on the side lying opposite the curved side a light-absorbing device, such as e.g. a trap aperture, which absorbs reflective beams or beams which pass through the feeds and discharges of the channel 2.1 out of the sample cell 1. These light beams are not to be taken into account for the measurement and distort the measurement result if they are collected by the light-sensitive detectors 5. The light beam 3 running along the channel 2 irradiates the colloidal suspension, and light is scattered by the molecules in all directions. The light beams 4 scattered at a specific angle are refracted towards the axis of incidence at the suspension/sample cell interface, and run in parallel through the sample cell 1. The light beams 4 scattered in a plane with the channel 2 (horizontal) are focused into the light-sensitive detectors 5 by the polished, round side of the sample cell 1 at the sample cell/surrounding medium interface, an aperture system 6 determining the angle range to be measured. The light beams 4 scattered in a plane perpendicular to the plane of the channel 2 (vertical) are also focussed by the polished, round side of the sample cell 1 so that the focussed beams 4 are collected by the light-sensitive detectors 5. The focusing can additionally be implemented by Fresnel lenses and/or cylindrical lenses. Fresnel lenses are compact optical lenses which are characterized by a division into annular steps. By means of the steps a constant focal width is achieved, i.e. the distance of the focal point or focus does not change. The characteristic shape of the Fresnel lenses makes it possible to save weight, due to which they are used in applications where weight is crucial. Cylinder lenses have different curvatures in two directions perpendicular to one another, i.e. in a narrower sense cylindrical lenses are sections of a cylinder. As a further embodiment, both types of lens can execute the focussing of the light beams scattered by the suspension and focus the latter into the detectors 5. Light beams which are produced by reflection and/or light scattering on the feed and discharge of the channel 2.1 are prevented from passing into the detectors by the aperture system 6 fitted to the light-sensitive detectors 5. The angle range to be measured is thus defined. By means of the vertical and horizontal focussing substantially all of the scattered light 4 which is produced by the irradiation of the colloidal suspension is fed into the light-sensitive detectors 5. The scattered volume to be measured is thus increased and the sensitivity improved.

LIST OF REFERENCE NUMBERS

1 Sample cell
2 Channel
2.1 Feed and discharge of the channel
3 Light beam
4 Light scattered by the suspension
5 Light-sensitive detectors
6 Aperture system
7 Curved surface/side
8 Non-curved surface/side

The invention claimed is:

1. A device for measuring light scattering properties of a suspension which is fed through a sample cell and is irradiated by a monochrome collimated light beam, the device comprising:
   a sample cell (1) has a channel (2) which permits feed and discharge of the suspension, and which allows a monochrome collimated light beam (3) to pass in, pass through and pass out in the direction of the channel length,
   wherein a cell geometry of the sample cell (1) displays a curved surface (7), and the sample cell is formed from transparent material and focuses light (4) scattered horizontally in a specific angle by a curved surface (7) of the sample cell (1) onto a point outside the sample cell to achieve focussed light, and
   wherein light-sensitive detectors (5) are arranged in the point onto which the light is focussed so that the light-sensitive detectors collect the focussed light (4) which is scattered by a suspension and which passes through the channel and the transparent material of the sample cell (1).

2. The device according to claim 1, wherein the cell geometry of the sample cell (1) has a curved surface (7), in particular of an ellipsoid, a hyperbolic, a parabolic shape or the form of a circle.

3. The device according to claim 1, wherein the sample cell has an optically polished surface and a cross-section of the sample cell (1) displays a curved surface (7) in a plane of the channel (2), and the channel (2) extends along an axis, the channel (2) being shorter than a smallest diameter of the curve.

4. The device according to claim 1, wherein the sample cell has a polished surface, and a cross-section of the sample cell (1) is curved in a plane perpendicular to the plane of the channel (2).

5. The device according to claim 1, wherein the sample cell is produced from glass, polymer or a combination of the aforementioned materials or a liquid.

6. The device according to claim 1, wherein light-sensitive detectors (5) are arranged over the curved surface (7) in a plane with the channel (2) and collect light (4) scattered by the suspension.

7. The device according to claim 1, wherein light is focussed on the curved surface (7) in a plane perpendicular to a plane of the channel (2), by means of a further curve or by means of Fresnel lenses and/or cylindrical lenses, and can be collected by light-sensitive detectors (5).

8. The device according to claim 1, wherein the light-sensitive detectors (5) have an aperture system (6) which defines an angle range to be observed provided a focus lies within the aperture.

9. The device according to claim 1, wherein there are no light-sensitive detectors arranged on a side (8) lying opposite the curved surface (7), and a light-absorbing device absorbs light which is not to be collected by the light-sensitive detectors.

10. The device according to claim 1, wherein the monochrome collimated light beam (3) has a cross-sectional dimension that is smaller than that of the channel.

11. A method for measuring light (4) scattered on molecules present in a suspension, the method comprising the steps of:
- a. feeding a suspension through a channel (2) that extends along an axis through a sample cell (1),
- b. running a collimated, monochrome light beam (3) along the channel,
- c. passing scattered light beams (4) running in parallel and scattered horizontally in a specific angle through the curved shape (7) of the sample cell (1),
- d. focussing the horizontally scattered light beams by the polished, curved shape of the sample cell (1) onto a point outside the sample cell to achieve focussed light, and
- e. collecting the focussed light by light-sensitive detectors (5) arranged horizontally and vertically to the channel (2), in the point onto which the scattered light is focussed.

12. The method according to claim 11, wherein
the sample cell (1) in the plane of the channel (2) and in a plane perpendicular to a plane of the channel (2) displays a curved surface (7).

13. The method according to claim 11, wherein
the light-sensitive detectors (5) are arranged over the curved shape (7) of the sample cell (1).

* * * * *